(12) United States Patent
Schuh

(10) Patent No.: US 6,886,452 B2
(45) Date of Patent: May 3, 2005

(54) SYSTEM AND METHOD OF LEAVENING WITH CARBON DIOXIDE MONITORING

(75) Inventor: William C. Schuh, Delavan, WI (US)

(73) Assignee: Claud S. Gordon Company, Richmond, IL (US)

( * ) Notice: Subject to any disclaimer, the term of this patent is extended or adjusted under 35 U.S.C. 154(b) by 217 days.

(21) Appl. No.: 09/935,904

(22) Filed: Aug. 23, 2001

(65) Prior Publication Data

US 2003/0039725 A1 Feb. 27, 2003

(51) Int. Cl.[7] .............................. A23L 1/00; A21D 8/00; A47J 27/00
(52) U.S. Cl. .............................. 99/327; 99/331; 99/344; 99/348; 99/468
(58) Field of Search ........................... 99/326–333, 348, 99/352, 467, 468, 473–476, 516, 483, 339, 340; 219/401, 400, 411, 412, 201, 494, 497; 126/20, 21 A, 20.1; 426/231–233, 243, 19; 312/27, 523, 236

(56) References Cited

U.S. PATENT DOCUMENTS

| | | | | |
|---|---|---|---|---|
| 3,518,949 A | * | 7/1970 | Stock | 99/468 |
| 4,164,643 A | * | 8/1979 | Peart et al. | 219/411 |
| 4,885,176 A | * | 12/1989 | Nakakura et al. | 426/19 |
| 4,903,587 A | * | 2/1990 | Nagasaka et al. | 99/325 |
| 5,352,606 A | | 10/1994 | Takano et al. | |
| 5,409,724 A | | 4/1995 | Heidolph et al. | |
| 5,433,139 A | * | 7/1995 | Kitagawa et al. | 99/327 |
| 5,492,702 A | | 2/1996 | Domingues | |
| 5,759,596 A | | 6/1998 | Domingues et al. | |
| 5,802,963 A | * | 9/1998 | Cohn et al. | 99/476 |
| 5,804,233 A | | 9/1998 | Lonergan et al. | |
| 5,925,397 A | | 7/1999 | Chung | |
| 5,939,109 A | | 8/1999 | Domingues et al. | |
| 6,323,464 B1 | * | 11/2001 | Cohn | 219/401 |

OTHER PUBLICATIONS

"The Leavening of Bread Dough" by Wayne R. Moore and R. C. Hoseney, *Cereal Foods World*, vol. 30, No. 11, p. 791–792 (Nov. 1985).

"A Review of Older and Some Newer Short–Time Bread Baking Studies" by P. L. Finney, *The Bakers Digest*, p. 81–86 (Oct. 1977).

* cited by examiner

*Primary Examiner*—Timothy F. Simone
(74) *Attorney, Agent, or Firm*—Harness, Dickey & Pierce, P.L.C.

(57) ABSTRACT

A system and method for monitoring carbon dioxide production during a dough leavening process to improve the efficiency and quality of the baking process. A yeast dough is placed in an oven for rising and baking. A carbon dioxide sensor is connected to the oven to sense the carbon dioxide in the oven atmosphere, and a monitoring device monitors the signal from the carbon dioxide sensor to provide an output indicative of the substantial end of the rising stage, and may automatically control the oven to begin baking.

19 Claims, 3 Drawing Sheets

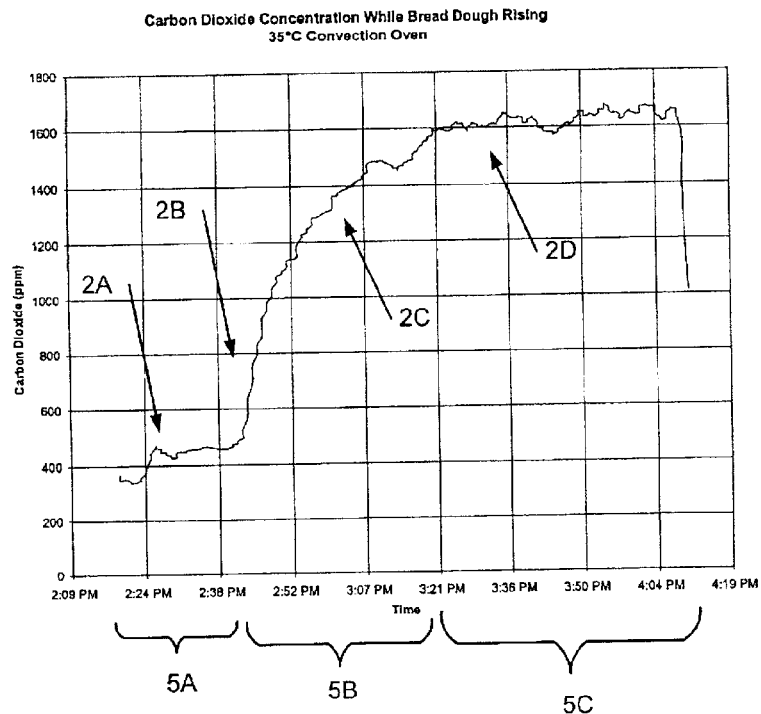
5A  5B  5C
Fig. 1
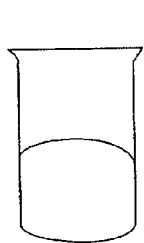 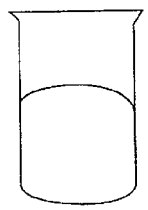 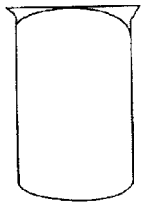 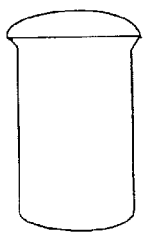
Fig. 2A    Fig. 2B    Fig. 2C    Fig. 2D

SYSTEM AND METHOD OF LEAVENING WITH CARBON DIOXIDE MONITORING

FIELD OF THE INVENTION

The present invention relates generally to the control of the bread making process by monitoring carbon dioxide created by the leavening process.

BACKGROUND OF THE INVENTION

The process of making bread or other leavened food products includes several stages including mixing, leavening and baking. During mixing, the baker mixes and blends flour with a leavening agent, such as yeast or a chemical leavening agent, sugar, salt, water, and/or other ingredients in accordance with a particular recipe to form a bread dough. An exemplary chemical leavening agent is baking powder, but most bread doughs use a yeast. Mixing generally is controlled by weight, volume, and time measurements.

After the mixing stage, the dough is allowed to rise during the leavening stage. Upon mixing, the leavening agent interacts with other ingredients to produce ethanol ($C_2H_5OH$) and carbon dioxide ($CO_2$). The ethanol provides a distinct flavor and odor while the carbon dioxide creates gas pockets inside the dough that allow the dough to rise and influence the finished texture of the bread. The leavening stage generally is controlled using a time and temperature (and possibly humidity) profile.

The leavening stage may include a fermentation phase and a proofing phase. Depending on the recipe, the fermentation phase may be repeated after a punching phase during which the dough is physically compressed before shaping the dough and allowing the dough to rise again in a second fermentation phase.

When the baker is satisfied with the amount the dough has risen, the baker bakes the bread, or other food product, at a higher temperature. As the dough begins baking, some of the yeast continues to generate additional gas and results in an additional stage of rising called ovenspring. Eventually the temperature of the dough reaches a point where yeast activity stops and no additional carbon dioxide is generated. The baking stage is controlled primarily by a time and temperature profile in an oven.

The amount or rate of production of carbon dioxide produced by various leavening agents generally changes over time. Differences in the amount or rate of carbon dioxide produced by various leavening agents has been used to select the optimum leavening agents for particular recipes. Chemical leavening agents generally produce carbon dioxide at a substantially constant rate, the amount and duration of the production generally being dependant on the amount of chemical leavening agent and reactants in the recipe.

The fermentation action of the yeast that results in carbon dioxide production varies with the yeast variety, recipe, temperature, and other factors. Thus, when yeast is used as the leavening agent, carbon dioxide production is more variable than when the baker uses a chemical leavening agent.

Common yeast fermentation times are on the order of several hours, and common proofing times are on the order of about one hour. Dough that spends too much or too little time in the fermentation or proofing phases may have undesirable characteristics. For example, over-fermentation can lead to the production of ascorbic acid from oxidation, which may change the flavor of a finished loaf of bread. Under-proofing results in tight grains, ripped-out break and shred and low loaf volume, while over-proofing leads to open grains, caps, and asymmetrical loaves of bread. Commercial baking systems process large numbers of baked goods, such as bread loaves, in large capacity ovens. Any reduction in the production time can lead to substantial savings either through increased throughput or reduced capital investment.

SUMMARY OF THE INVENTION

It is a purpose of this invention to provide a control means that uses the carbon dioxide levels as a control parameter in a dough leavening process. The present invention provides a system and method for monitoring carbon dioxide production during a dough leavening stage to improve the efficiency and quality of the baking process, particularly for a yeast dough, and more particularly for a bread dough. As a result, the present invention helps to control several characteristics of the finished baked product and improves the efficiency of the baking process.

According to one embodiment of the invention, a system for making a leavened food product from a dough having a leavening agent that can produce carbon dioxide includes the following elements. First, a carbon dioxide sensor for monitoring the carbon dioxide produced by the leavening agent and for providing an output indicative of the carbon dioxide produced. And second, a monitor connected to the carbon dioxide sensor for providing an output based on input from the carbon dioxide sensor.

The monitor may be configured to provide an indication of the amount of carbon dioxide, or the rate of carbon dioxide production. In addition, the system may include a container, such as an oven or a proofing oven, within which the dough is placed. The carbon dioxide sensor is exposed to the atmosphere within the container, and may be mounted within the container.

The system may further include a temperature sensor connected to the container for measuring the temperature in the container. The temperature sensor provides an output indicative of the temperature in the container, and that output may be directed to an indicator or any type of output device. The temperature sensor may be one or more of a thermometer, a thermocouple, a thermistor, or an infrared (IR) detector.

The monitor may further include a controller, such as a general purpose processor or a digital signal processor, interconnecting the carbon dioxide sensor and the indicator. Thus the monitor can control the indicator in response to information or data received from the carbon dioxide sensor. The system may also include one or more temperature and humidity regulators, for regulating the temperature and humidity, respectively, in the oven. The monitor also can control the temperature and humidity regulators, including automatically baking the dough upon detecting a certain point in the leavening process as indicated by the carbon dioxide sensor.

One method of baking a leavened food product includes the following steps: mixing ingredients that include a leavening agent to form a dough; placing the dough in a container; providing conditions in the container that allow the leavening agent to form carbon dioxide; monitoring the carbon dioxide; and controlling further processing of the dough based on the production of carbon dioxide by the leavening agent. Monitoring may include signaling a transition from an active stage of increasing carbon dioxide production to a stable stage of relatively constant carbon dioxide production. Mixing includes mixing ingredients, including yeast, to form a bread dough.

Further processing of the dough includes punching and shaping of the dough, as well as baking the dough.

A system in accordance with the present invention also may be described as including means for monitoring the carbon dioxide produced by the leavening agent and for providing an output indicative of the carbon dioxide produced; and means for providing a signal based on input from the means for monitoring.

The means for providing may include means for analyzing the input from the means for monitoring, and means for identifying a transition from an active stage of carbon dioxide production to a stable stage of carbon dioxide production.

The foregoing and other features of the invention are hereinafter fully described and particularly pointed out in the claims, the following description and annexed drawings setting forth in detail a certain illustrative embodiment of the invention, this embodiment being indicative, however, of but one of the various ways in which the principles of the invention may be employed.

BRIEF DESCRIPTION OF THE DRAWINGS

FIG. 1 is a graph of carbon dioxide production in a bread dough leavening process overtime.

FIGS. 2A–2D are schematic illustrations of rising bread dough at approximate times corresponding to points 2A–2D, respectively in FIG. 1.

DETAILED DESCRIPTION

Figure 3:
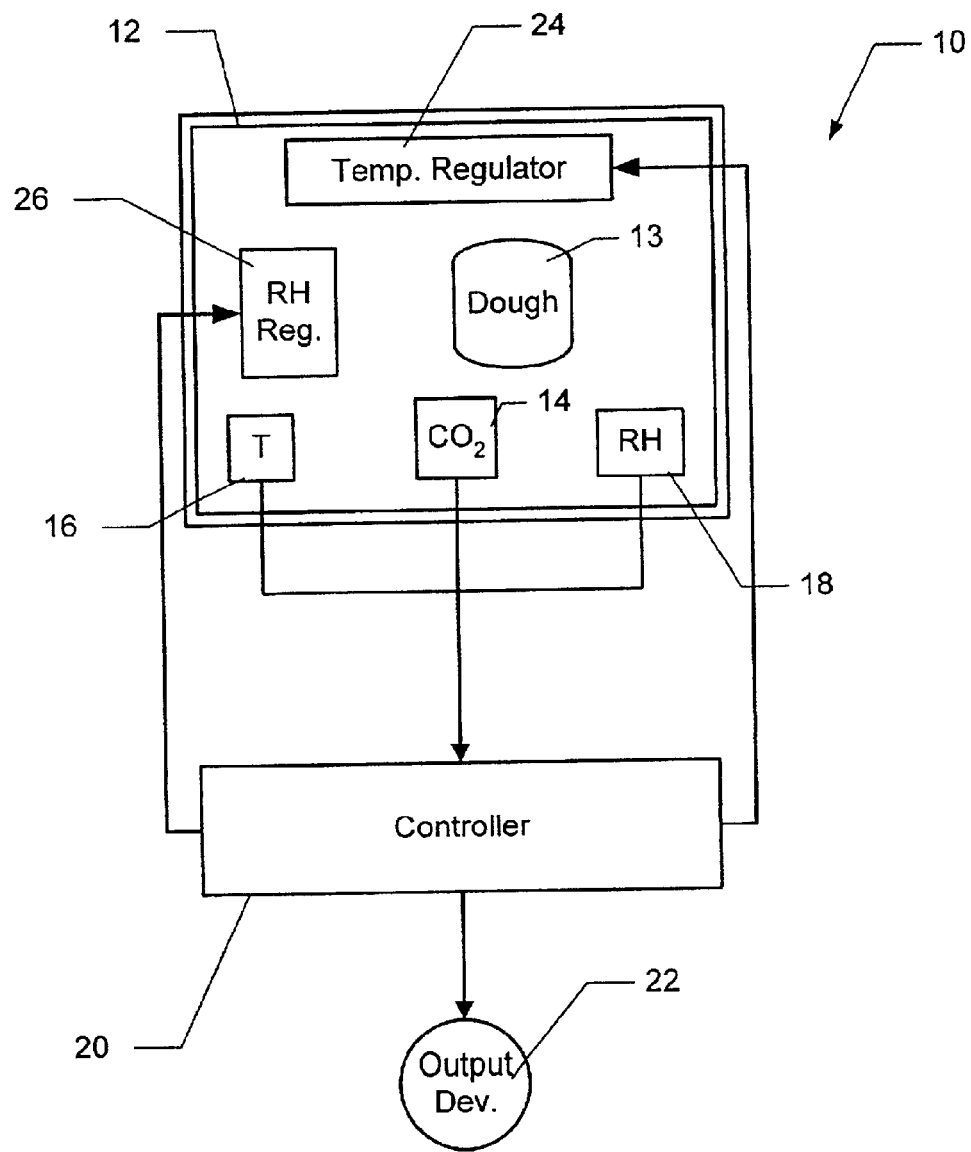
FIG. 3 is a schematic illustration of a system in accordance with the present invention.

The present invention provides a system and method for monitoring carbon dioxide production during a dough leavening stage to improve the efficiency and quality of the process of making a leavened food product, such as bread. A baker generally places the dough in an oven or other container for rising and baking. The system includes a carbon dioxide sensor that senses the carbon dioxide in the oven atmosphere, and a monitoring device that monitors the signal from the carbon dioxide sensor to provide an output indicative of the substantial end of the dough's rising, and may automatically control the oven to begin baking.

While time and temperature-based control methods have been successful in producing quality bread for centuries, such methods do not rely on measurements of the fundamental process that is occurring. That is, current methods do not measure the carbon dioxide production as a control parameter. In addition to reducing process time, improved control can also improve the quality of the bread. Although the system and method provided by the invention will be described with reference to yeast in bread dough, such a system and method may be equally applicable to any baked goods using a leavening agent, particularly a yeast.

Fermentation of carbohydrates (in the form of sugar or flour) by yeast generally occurs through the following reaction.

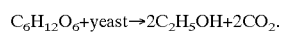

$$C_6H_{12}O_6 + \text{yeast} \rightarrow 2C_2H_5OH + 2CO_2.$$

It has been experimentally determined that approximately one thousand ninety-seven cubic centimeters (1097 cc) of carbon dioxide is generated by yeast action per one hundred grams (100 g) of flour. Of that amount, approximately four hundred twenty-five cubic centimeters (425 cc) are retained in the dough, with the rest being lost to the environment. Of the approximately six hundred and seventy-two cubic centimeters (672 cc) lost, fifty-six cubic centimeters (56 cc) are lost during surface diffusion in the fermentation process and mixes with the carbon dioxide in the atmosphere.

The data graphically shown in FIG. 1, was taken from a fifty-three centimeter by forty centimeter by forty-three centimeter (53 cm×40 cm×43 cm) convection oven (having a volume of ninety-three and six tenths times ten to the third cubic centimeters ($93.6 \times 10^3$ cc)) with a three hundred gram (300 g) flour dough that would be expected to produce one hundred sixty-eight cubic centimeters (168 cc) of carbon dioxide in the oven (see also FIG. 2A). Standard dry air generally has a nominal composition of approximately three hundred to four hundred parts per million (300–400 ppm) of carbon dioxide. This agrees within experimental error with the values shown in FIG. 1.

With the one hundred sixty-eight cubic centimeters (168 cc) of carbon dioxide given off by the fermenting dough through surface diffusion during the fermentation process, approximately eighteen hundred parts per million (1800 ppm) of carbon dioxide would be released into the oven. As shown in the graph in FIG. 1, this value agrees with the experimental data within generally accepted limits of error.

The graph of FIG. 1 can be divided into three distinct sections, 5A, 5B and 5C. In the early section 5A the carbon dioxide level is stable at a value near the level of standard air, 400 ppm (see also FIG. 2A). Then as the yeast activity progresses into the middle section 5B the carbon dioxide diffuses from the surface of the dough rapidly increasing the level of carbon dioxide and causing the dough to rise or increase in volume. (See FIG. 2B.) Finally in the last section 5C the carbon dioxide level stabilizes as the yeast activity slows and reaches an equilibrium condition slowing the volumetric increase of the dough. (See FIGS. 2C and 2D.) These three zones will be referred to as the early, active and stable zones, 5A, 5B, 5C, respectively. Different strains of yeast produce different amounts of carbon dioxide at different rates and for different periods of time, but generally still have early, active and stable zones. A yeast that produces carbon dioxide at a slower rate in a longer active zone may be preferred for a particular recipe, for example.

By monitoring the carbon dioxide levels, the baker has a better indication of the doneness of the fermentation and proofing processes. This provides a better level of control than standard time and temperature recipes. In addition, faulty dough mixes can be detected earlier from an unusual level of carbon dioxide, such as from yeast inactivity. The carbon dioxide levels (the cumulative or total amount of carbon dioxide) and the first derivative with respect to time (the rate a certain amount of carbon dioxide is produced over time) are used as indicators of the doneness of the dough rising or leavening process. When the carbon dioxide level transitions from the active zone 5B to the stable zone 5C, the dough has substantially finished rising and further time will not add significantly to the dough volume. The baker may then choose to remove the dough or to continue the fermentation or proofing stage for reasons other than dough volume increase.

An exemplary system 10 provided by the invention is illustrated in FIG. 3. The system includes a space or container 12 within which dough 13 is placed for the fermentation and proofing stages, such as an oven. A carbon dioxide sensor 14, and any other desired sensor, including the illustrated temperature and humidity sensors 16, 18, respectively, are connected to the oven 12 to monitor the conditions therein. The sensors may be mounted inside the oven, or the sensors may be mounted remotely if a sampling tube or other means is provided to convey the oven atmosphere to the sensor.

The system also includes a monitor 20 connected to the sensors to monitor the output of the sensors and to provide an output based on input from the sensors, such as a visual or audible signal indicating the change from the active zone 5B to the stable zone 5C (FIG. 1). The illustrated system also includes a separate means 22 for providing an output, including an output device such as a speaker or electronic display, although alternatively such means may be integral with the monitor. The monitor and output device may be an integral part of the sensor and may perform additional functions.

The monitor 16 may also function as a controller that provides an output in the form of a control signal for controlling means for regulating the temperature and/or humidity (generally relative humidity) 24 and 26, respectively, for example, within the oven. The controller, temperature regulator and humidity regulator provide the ability to automate the bread making process based on the level of carbon dioxide. For example, when the yeast activity reaches the stable zone 5C (FIG. 1), the monitor may automatically send a control signal to the temperature regulator to raise the temperature in the oven to a baking temperature. Thus, the monitor can automatically control the transition between the proofing and baking stages, and improve the efficiency and quality of the baking process.

The carbon dioxide sensor 14 may be a commercially available sensor including an infrared (IR) detector such as the model 302D5RU from Digital Control Systems of Portland, Oreg. The IR sensor utilizes the absorption of infrared radiation by carbon dioxide as a means of measurement. The output of the sensor is available in several versions including a 0–1VDC analog signal that will have a linear correlation to the 0 to M level of carbon dioxide, where M is a function of the specific sensor. This analog signal can be connected to one or more processors, including general purpose processors or digital signal processors, such as the Watlow 922 PID control from Watlow of Winona, Minn. The processors may be programmable to provide flexibility in the design of the system, and may be programmed with an expected chart of carbon dioxide production against which measurements taken by the sensor can be compared, such as is shown in FIG. 1.

When the dough 13 is placed into the oven 12, the initial carbon dioxide levels will be near the standard atmospheric level of about 400 ppm. As the yeast activity increases, the carbon dioxide level will increase as shown in the active zone 5B of FIG. 1. The concentration of carbon dioxide will rise at a rate between about 10 and about 100 ppm/min in the active region, generally dependent on the recipe and oven environment. In FIG. 1 the value is about 90 ppm/min. At the end of the significant dough increase the carbon dioxide level will transition from the active zone 5B to the stable zone 5C (FIG. 1). The monitor analyzes the data from the carbon dioxide sensor to determine when this point (or any other desirable point in the process) has occurred, based on a measurement of a predetermined amount of carbon dioxide produced or a change in the rate of carbon dioxide production, for example. Thus the monitor can generate a signal that is sent to the indicator to indicate completion of the leavening stage, for example. The system thus provides the baker with an indication of the transition from an active yeast stage to a stable aging stage. This generally indicates an optimum time to begin baking the dough. The system may also provide the baker with an indication of any irregularities, such as insufficient or excessive carbon dioxide production.

Depending on the recipe, the dough may be allowed to remain in the oven for a period following the indicated end of the active zone 5B (FIG. 1). This additional time may be used by the baker to enhance some of the flavor and texture parameters of the finished bread through surface treatments and/or the addition of further ingredients.

The monitor, if it has the ability to function as a controller, may be programmable to automatically instruct the means for heating the oven to elevate the temperature in the oven to a baking temperature. The monitor may also automatically control the time and temperature for the baking stage and provide a signal indicating the end of the baking stage.

Figure 4:
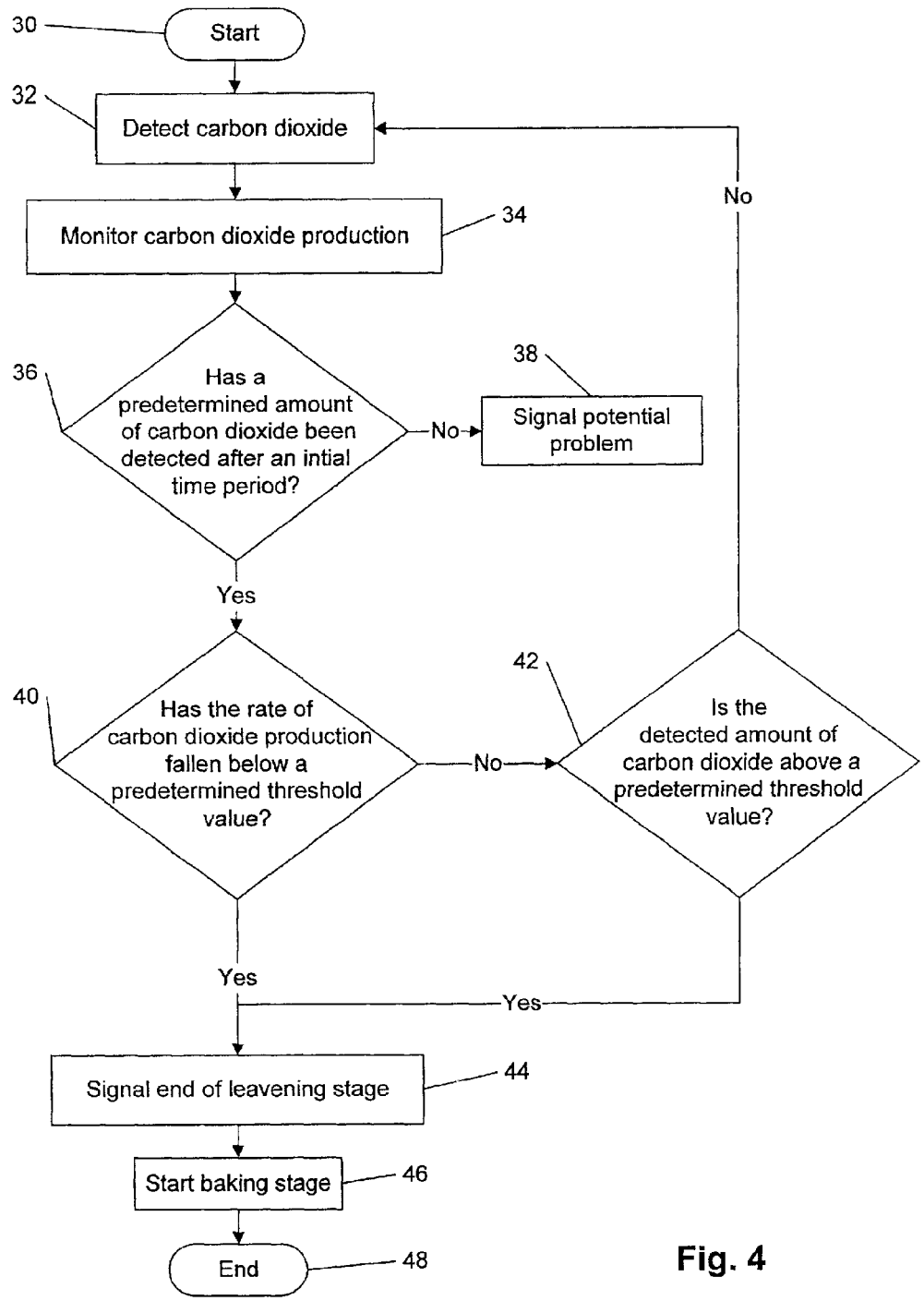
FIG. 4 is a flowchart illustrating the steps of one method in accordance with the present invention.

One embodiment of the method of the invention is illustrated in the flowchart shown in FIG. 4. At the start in step 30, the dough is placed in the oven. In step 32 the carbon dioxide sensor detects carbon dioxide in the oven. The carbon dioxide production is monitored in step 34.

At step 36, the monitor makes a decision whether a predetermined amount of carbon dioxide has been detected after an initial time period. For example, to determine whether the yeast is producing sufficient carbon dioxide. If no, then in the next step, step 38, signals a potential problem to alert the baker that the yeast may not be acceptable. If yes, then the next step is to determine whether the rate of carbon dioxide production has fallen below a predetermined threshold value, as happens at the end of the active zone 5B shown in FIG. 1. If no, then in step 42 the monitor determines whether the detected amount of carbon dioxide is above a predetermined threshold value, another measure of whether the leavening stage is complete. If no, then the method returns to step 32 and continues to detect and monitor the carbon dioxide. If yes, either at step 40 or step 42, the next step is to signal the end of the leavening stage at step 44. Alternatively, one of steps 40 and 42 may be omitted, although using both provides some redundancy in the system. As a further alternative, the monitor may be programmed to compare the detected carbon dioxide as a function of time against a predetermined acceptable curve of carbon dioxide concentration over time, such as is shown in FIG. 1. A comparison of the concentration of carbon dioxide as a function of time against the detected carbon dioxide can be used to detect irregularities in the production of the carbon dioxide, and to determine the specific points of interest, such as the end of the leavening stage.

At the end of the leavening stage, signaled at step 44, the system automatically proceeds to step 46 and begins the baking stage. Step 46 may be omitted and the method may end after step 44, otherwise the method ends at the completion of the baking stage at step 48.

As described above and shown in the illustrated embodiment, the present invention provides a significant improvement over the state of the art. Rather than relying on a time and temperature profile, the illustrated system monitors the carbon dioxide production to provide more consistency in the quality of the baked goods produced, as well as improving the efficiency of the baking process.

Although the invention has been shown and described with respect to a certain illustrated embodiment, equivalent alterations and modifications will occur to others skilled in the art upon reading and understanding the specification and the annexed drawings. In particular regard to the various functions performed by the above described integers (components, assemblies, devices, compositions, etc.), the terms (including a reference to a "means") used to describe such integers are intended to correspond, unless otherwise indicated, to any integer which performs the specified function (i.e., that is functionally equivalent), even though not structurally equivalent to the disclosed structure which performs the function in the herein illustrated embodiment of the invention.

What is claimed is:

1. A system for making a leavened food product from a dough having a leavening agent that can produce carbon dioxide, the system comprising:
   a carbon dioxide sensor for detecting carbon dioxide produced by the leavening agent and for providing an output indicative of the carbon dioxide produced; and
   a monitor connected to the carbon dioxide sensor for providing a signal based on input from the carbon dioxide sensor, where the signal indicates a cumulative amount of carbon dioxide produced and a rate of carbon dioxide production.

2. A system for making a leavened food product from a dough having a leavening agent that can produce carbon dioxide, the system comprising:
   a carbon dioxide sensor for detecting carbon dioxide produced by the leavening agent and for providing an output indicative of the carbon dioxide produced;
   a monitor connected to the carbon dioxide sensor for providing a signal based on input from the carbon dioxide sensor, where the signal indicates at least one of (a) a cumulative amount of carbon dioxide produced and (b) a rate of carbon dioxide production; and
   a container within which the dough is placed, the carbon dioxide sensor being exposed to the atmosphere within the container.

3. A system as set forth in claim 2, wherein the carbon dioxide sensor is mounted within the container.

4. A system as set forth in claim 2, further comprising a temperature sensor connected to the container for measuring the temperature in the container and for providing an output indicative of the temperature.

5. A system as set forth in claim 4, wherein the temperature sensor is connected to an indicator for providing an output in response to the input from the temperature sensor.

6. A system as set forth in claim 4, wherein the temperature sensor is selected from a group that includes a thermometer, a thermocouple, a thermistor, and an infrared (IR) detector.

7. A system as set forth in claim 2, wherein the container includes an oven.

8. A system as set forth in claim 2, wherein the container includes a proofing oven.

9. A system for making a leavened food product from a dough having a leavening agent that can produce carbon dioxide, the system comprising:
   a carbon dioxide sensor for detecting carbon dioxide that outputs a signal indicative of the carbon dioxide produced; and
   a monitor connected to the carbon dioxide sensor,
   wherein the monitor includes an indicator for providing an output based on input from the carbon dioxide sensor and a controller interconnecting the carbon dioxide sensor and the indicator, the controller controlling the indicator in response to data received from the carbon dioxide sensor.

10. A system as set forth in claim 9, further comprising a temperature sensor connectable to the controller and a temperature regulator that regulates the temperature connected to and controlled by the controller, the controller controlling the temperature regulator in response to data received from the carbon dioxide sensor and the temperature sensor.

11. A system as set forth in claim 9, further comprising a humidity sensor connectable to the controller and a humidity regulator that regulates the humidity connected to and controlled by the controller, the controller controlling the humidity regulator in response to data received from the carbon dioxide sensor and the humidity sensor.

12. A system as set forth in claim 9, wherein the controller includes a digital signal processor.

13. A system as set forth in claim 9, wherein the controller controls the time and the temperature for baking the dough to produce the leavened food product based on input from the carbon dioxide sensor.

14. A system as set forth in claim 9, wherein the monitor is configured to provide an indication of a cumulative amount of carbon dioxide produced.

15. A system as set forth in claim 9, wherein the monitor is configured to provide an indication of the rate of carbon dioxide production.

16. A system for making a leavened food product from a dough having a leavening agent that can produce carbon dioxide, the system comprising: means for monitoring the carbon dioxide produced by the leavening agent and outputting a signal indicative of at least one of (a) cumulative amount of carbon dioxide produced and (b) a rate of carbon dioxide production; and
   means for providing an output based on input from the means for monitoring.

17. A system as set forth in claim 16, wherein the means for providing includes means for analyzing the input from the means for monitoring.

18. A system for making a leavened food product from a dough having a leavening agent that can produce carbon dioxide, the system comprising:
   means for monitoring the carbon dioxide produced by the leavening agent and outputting a signal indicative of the carbon dioxide produced; and
   means for providing an output based on input from the means for monitoring that includes means for analyzing the input from the means for monitoring;
   wherein the means for analyzing includes means for identifying a transition from an active stage of carbon dioxide production to a stable stage of carbon dioxide production.

19. A system for making a leavened food product from a dough having a leavening agent that can produce carbon dioxide, the system comprising:
   a carbon dioxide sensor for detecting carbon dioxide produced by the leavening agent and for providing an output indicative of the carbon dioxide produced; and
   a monitor connected to the carbon dioxide sensor for providing a signal based on input from the carbon dioxide sensor, where the signal indicates a rate of carbon dioxide production.

* * * * *